United States Patent [19]
Gevins et al.

[11] Patent Number: 5,331,970
[45] Date of Patent: Jul. 26, 1994

[54] EEG SPATIAL ENHANCEMENT METHOD AND SYSTEM

[75] Inventors: Alan S. Gevins, San Francisco; Jian Le, Daly City, both of Calif.

[73] Assignee: SAM Technology, Inc., San Francisco, Calif.

[21] Appl. No.: 868,724

[22] Filed: Apr. 14, 1992

Related U.S. Application Data

[63] Continuation-in-part of Ser. No. 578,880, Sep. 7, 1990, Pat. No. 5,119,816.

[51] Int. Cl.$^5$ .................................................. A61B 5/04
[52] U.S. Cl. ........................................................ 128/731
[58] Field of Search ........................ 128/731, 732, 644

[56] References Cited
U.S. PATENT DOCUMENTS

| | | | |
|---|---|---|---|
| 4,416,288 | 11/1983 | Freeman | 128/731 |
| 4,736,751 | 4/1988 | Gevins et al. | 128/731 X |
| 4,967,038 | 10/1990 | Gevins et al. | 128/731 X |
| 5,038,782 | 8/1991 | Gevins et al. | 128/731 |
| 5,119,816 | 6/1992 | Gevins | 128/644 |

*Primary Examiner*—Lee S. Cohen
*Assistant Examiner*—Jeffrey R. Jastrzab
*Attorney, Agent, or Firm*—Eliot S. Gerber

[57] ABSTRACT

In an electroencephalographic (EEG) system and method the subject's brain waves are recorded using electrodes removably connected to the scalp. The spatial resolution may be improved, in one embodiment, by "Deblurring", based on digital computer processing measurements of the positions of the electrodes; measurements of the subject's head size, shape, scalp thickness, skull thickness and brain shape; and estimates of the conductivity of the skull, scalp and cerebral spinal fluid.

13 Claims, 9 Drawing Sheets

EEG SPATIAL ENHANCEMENT METHOD AND SYSTEM

This invention was made with Government support under Grants R44-MH-27525, R44-NS27392 R01-MH43324 and R01-NS23550 awarded by the Alcohol, Drug Abuse and Mental Health Administration and the National Institutes of Health. The Government has certain rights in the invention.

RELATED APPLICATION

This application is a continuation-in-part application partly based on U.S. application Ser. No. 07/578,880, filed Sep. 7, 1990 and now U.S. Pat. No. 5,119,816.

BACKGROUND OF THE INVENTION

1. Field of Invention

The invention relates to medical systems and methods and more particularly to an electroencephalograph (EEG) system and method having improved spatial resolution.

2. Related Art

Electroencephalography (EEG) is a noninvasive technique for monitoring brain function based on amplification of brain potentials recorded at the scalp. Although the EEG has been measured for over 60 years, its full potential as a technology for imaging brain function has not yet been realized. Its chief advantages, when compared with other brain imaging technologies, such as positron emission tomography (PET) are: (1) an unsurpassed millisecond-level temporal resolution necessary for resolving sub-second neurological processes; and (2) simplicity of the sensors (essentially a small piece of metal and an operational amplifier) which results in low cost and ability to record for prolonged periods of time in a naturalistic setting. The chief disadvantage of the traditional EEG method is poor spatial resolution. There are only two obstacles to substantially improving spatial resolution. The first is that more scalp recording sites are needed. While it is the usual clinical practice to record EEG from 19 sites, it has been demonstrated with recordings from up to 124 sites that additional spatial information is available. U.S. Pat. No. 4,736,751, incorporated by reference, describes a system using a larger number of electrodes and various digital computer based methods to obtain more information from the brain wave signals. U.S. Pat. Nos. 4,967,038, 5,038,782 and [patent to issue on U.S. Ser. No. 07/578,880], incorporated by reference, describe systems for conveniently obtaining EEG recordings from a larger number of electrodes and locating their positions. The second obstacle is that spatial enhancement procedures are needed to reduce blur distortion that occurs as electrical potentials generated in the brain at the microvolt level are volume conducted through brain, cerebral spinal fluid, the low-conductivity skull, and scalp to the recording electrodes at the scalp surface. However, spatial enhancement is possible since the 3 dB point of the point spread function for conductance of potentials from the brain surface to the scalp averages about 2.5 cm and with 128 electrodes spaced evenly on an average adult head, the interlectrode distance is about 2.25 cm.

U.S. Pat. No. 4,416,288 to Walter Freeman entitled "Apparatus And Method For Reconstructing Subsurface Electrophysiological Patterns" discusses, in an EEG system, calculation of spatial deconvolution transformation of the detected electrode field potentials. However, no attempt is made to actually measure the shape and thickness of the scalp and skull of the subject, or the actual positions of the electrodes on the scalp, or to correct the potentials for distortion due to transmission through the skull and scalp.

SUMMARY OF THE INVENTION

A functional-anatomical brain scanner with a temporal resolution of less than a hundred milliseconds measures the neural substrate of higher cognitive functions, as well as diagnosing seizure disorders. Electrophysiological techniques, such as electroencephalograms (EEGs), have the requisite temporal resolution but their potential spatial resolution has not yet been realized. Progress in increasing the spatial detail of scalp-recorded EEGs and in registering their functional information with anatomical models of a patient's brain has been inhibited by the lack of a convenient means of rapidly placing many electrodes on the scalp, determining their location, determining the local thickness and conductivity of the scalp and skull, incorporating this information into a mathematical model, and using the mathematical model to enhance the spatial detail of the EEG signals. In the present invention, the three-dimensional positions of each electrode and the shape of the head are determined, the local thickness and conductivity of the skull and scalp are determined, and this information is used to reduce blur distortion of scalp-recorded EEGs, in effect mathematically placing the electrode just above the surface of the brain.

In accordance with the present invention, a method is presented to improve the spatial resolution of electroencephalograph (EEG) medical images using a realistic biophysical model of the passive conducting properties of each subject's head to estimate an electrical potential distribution at the cortical surface. A procedure, called "Deblurring", reduces spatial blur distortion of scalp-recorded EEGs due to transmission through the skull and other tissues. Deblurring estimates potentials at the superficial cerebral cortical surface from EEGs recorded at the scalp using a finite element or surface integral model of each subject's scalp, skull and cortical surface constructed from their Magnetic Resonance Images (MRIs) or from other measurement means such as mechanical measurement of the shape of the outside of the head and ultrasonic measurement of thickness of thescalp and skull. The Deblurring procedure requires: (1) measuring the size and shape of the subject's head; (2) measuring the local scalp and skull thickness; (3) estimating the local conductivity of the skull; and (4) using these measurements in a mathematical model of the head to correct the EEG signals for distortion.

BRIEF DESCRIPTION OF THE DRAWINGS

In the drawings:

FIG. 1a shows the original and FIG. 1b shows the deblurred evoked potentials (EPs) elicited by a stimulation. The data are mapped onto a computer model of the subject's head derived from his magnetic resonance image (MRI) and show the improvement in spatial detail produced by deblurring.

FIGS. 3a–3d show automated construction of finite elements within brain, skull and scalp volumes, with alternating elements shown for the respective tissue type.

FIG. 4 shows a block schematic diagram of the Deblurring method. The initial estimate of the cortical potentials, G (x, y, z) is the starting point for the loop contained inside the large frame. Using the estimated cortical potentials and the volumetric finite elements, the finite element method generates a forward solution of Maxwell's equation and produces an estimate of the scalp potentials. The goodness of fit of the estimated scalp potentials with respect to the actual scalp data is evaluated. If the goodness of fit is acceptable, the method has converged and ends. If it is not acceptable, the multidimensional optimization scheme searches for a new estimate of the cortical potentials, and the loop repeats until convergence is achieved. The round corner boxes represent the procedures and the rectangular boxes represent the intermediate data sets. The boxes outside of the large frame are the fixed data sets for the loop.

FIGS. 5a1, 5a2, 5b1 and 5b2 are perspective views of a patient showing the top of the brain exposed and showing 15-Hz steady-state somatosensory evoked potentials (EPs) elicited by stimulation of right-hand fingers. The patient was an epileptic patient who was a candidate for surgical treatment of her seizures. (a) Isopotential map of the original EP on the scalp surface (FIG. 5a1) and the deblurred EP computed on the cortical surface (FIG. 5a2). The brain, skull and scalp surfaces were constructed from horizontal magnetic resonance images obtained prior to surgery, one of which is shown in part between the scalp and cortex (FIG. 5a1). The small cylinders on the scalp surface represent the recording electrodes. The single large potential maxima in the scalp topography is more clearly defined in the deblurred data, which in addition shows some polarity reversals not visible in the scalp potential distribution. (b) The EP recorded directly on the brain surface is shown (FIG. 5b2) with the small cylinders representing the electrodes of the recording grid. The deblurred EP is shown again (FIG. 5b1) for comparison. The area covered by the grid shows a single large peak similar to that in the deblurred potentials. (c) FIGS. 5c1–5c3 show the effect of varying the scalp/skull conductivity ratio (r) on the deblurred data of FIGS. 5b1. The standard (80), and ratios which are $+/-50\%$ of the standard (40 to 120) are shown. There is not much difference in topography between t=40 and t=80. The topography appears more diffuse and the fine detail changes somewhat for t=120, which models the skull with the smallest conductivity value.

FIGS. 6a1, 6a2, 6a3, 6b1 and 6b2 are top plan views of cross-sections of a head. FIGS. 6a1–6a3 show deblurred steady-state evoked potentials (EPs) elicited by 15-Hz simulation of left middle, right middle and right index fingers of a normal subject. All three cases show the expected contralateral maximum in activity, while the response to right index finger stimulation differs markedly from that for the right middle finger. FIGS. 6b1 and 6b2 show original (FIG. 6b1) and deblurred (FIG. 6b2) EPs of the same subject in response to 15-Hz stimulation of left middle and right index fingers. The white dots (FIG. 6b1) represent the 122 scalp recording positions. The increase in spatial detail produced by the Deblurring procedure is apparent. The improvement in spatial detail as compared with the Laplacian Derivation of the same data (FIG. 1b) is also evident.

DETAILED DESCRIPTION

Electrical currents generated by sources in the brain are volume conducted through brain, cerebral spinal fluid, skull and scalp to the recording electrodes. Because of this, potentials due to a localized source are spread over a considerable area of scalp and the potential measured at a scalp site represents the summation of signals from many sources over much of the brain. In accordance with the current invention, two spatial enhancement methods are described which correct this blur distortion. Both methods use a realistic model of the shape of the head, and neither method requires specification of an arbitrary source model (e.g., current dipoles).

The simpler method computes an accurate estimate of the surface Laplacian Derivation (LD), which is proportional to local normal current at the scalp. This has the advantage of eliminating the effect of the reference electrode used for recording, and of eliminating much of the common activity due to either the reference electrode or volume conduction from distant sources. The disadvantages are that the LD does not produce valid values at the outermost ring of electrodes and it does not correct for local differences in skull thickness and conduction properties. The most accurate surface LD uses the actual measured electrode positions, and estimates the LD over the actual shape of the head using a 3-D spline algorithm.

According to a method called Deblurring, a further reduction in distortion can be obtained using a finite element or boundary integral model of the cortex, cerebral spinal fluid, skull and scalp to estimate the potentials which would actually be recorded on the surface of the brain. Deblurring is a "downward continuation" method in that, without prior knowledge or assumptions about the generating sources, the cortical potential distribution is derived given the scalp potential distribution and a realistic model of the conducting volume between the scalp and cortical surfaces. In the preferred implementation of Deblurring, a transformation matrix is constructed based on the geometry and conductivities of the finite elements which predicts the cortical potentials for any given set of scalp potentials.

For either procedure, a means is needed to align the EEG electrode positions with the outside surface of the scalp. Accordingly, according to the current invention, x, y, z translation and x, y, z axis rotations are computed iteratively to align the measured or computed positions of the EEG electrodes with the external surface of the scalp measured by a magnetic resonance image (MRI), computerized tomographic or ultrasonic scan, or mechanically. This alignment is done for each electrode by finding the distance to the closest point on the scalp surface and minimizing the mean distance for all electrodes. With MRIs that have a 3 mm inter-slice spacing, a mean error distance of better than 2 mm is achieved.

Figure 5A:
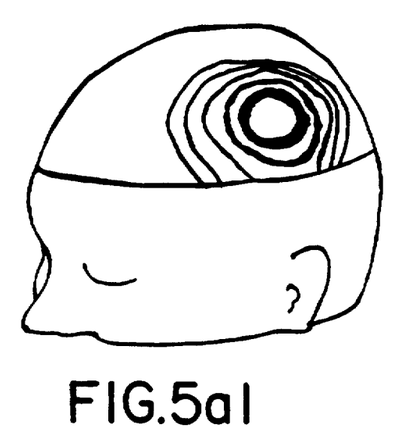
Figure 5A:
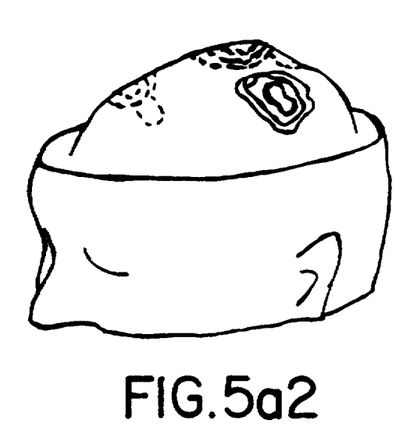
Figure 5B:
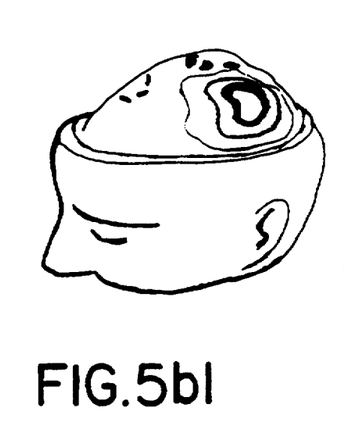
Figure 5B:
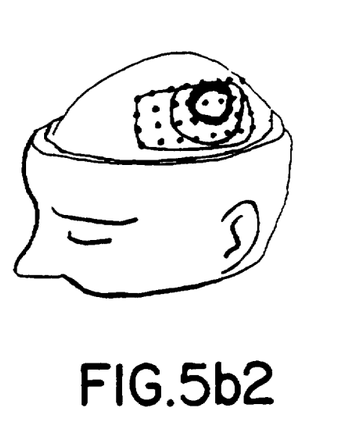
Figures 5C, 5C, 5C:
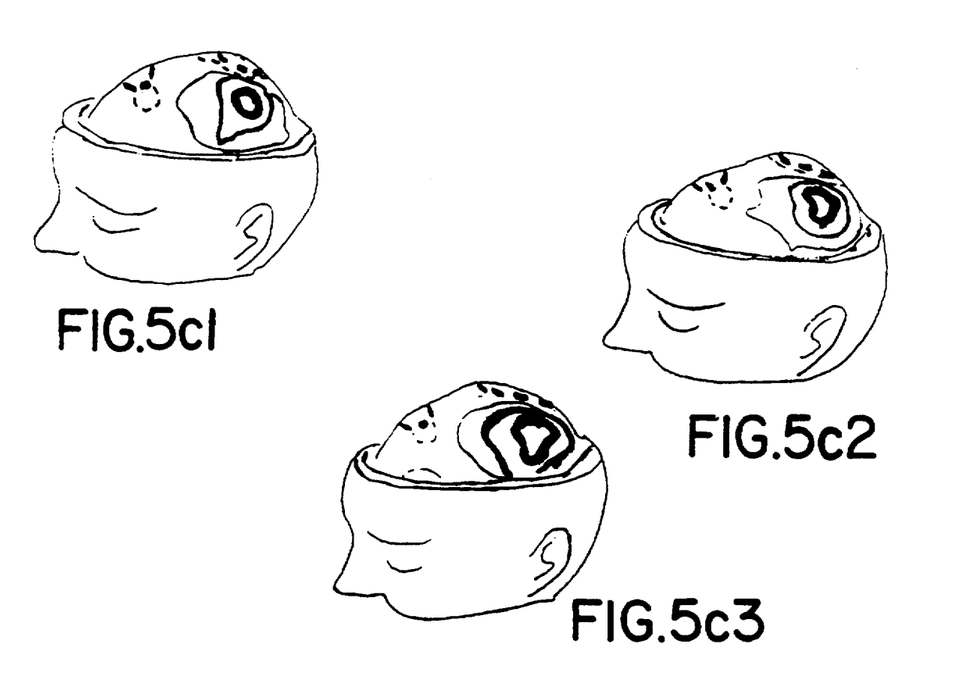
Figures 6A, 6A, 6A:
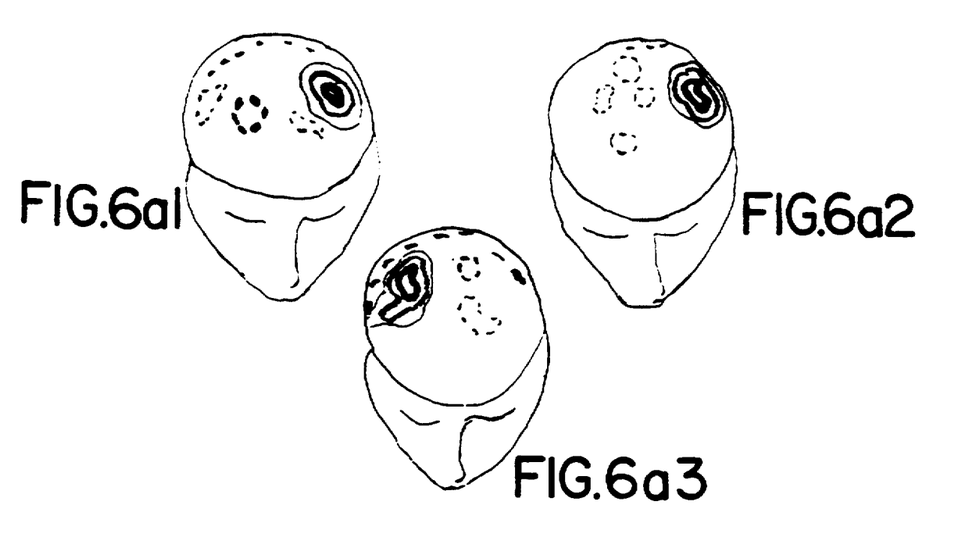

This is more accurate and less subjective than alignment procedures that use skull landmarks such as the nasion and pre-auricular points located visually in the MRI. FIGS. 5a (left) and 6b (left) show the electrodes displayed schematically on a scalp surface reconstructed from horizontal MRI scalp contours.

THREE-DIMENSIONAL SPLINE LAPLACIAN DERIVATION METHOD

3-D spline Laplacian Derivation

This section describes a new implementation of a common means for achieving spatial enhancement of the EEG signals using a Laplacian operator. Distortion of neuroelectric signals recorded at the scalp occurs principally because transmission through the low-conductivity skull acts as a spatial low-pass filter. A well-known signal processing technique to enhance higher spatial frequencies is to estimate the rate of change in the signal over a small distance using the Laplacian operator, the discrete approximation of which is referred to as the Laplacian Derivation. The original implementation of the Laplacian Derivation modeled the scalp surface as a plane and calculated a simple second-order finite difference from a rectangular array of equally-spaced electrodes. Spherical and ellipsoidal models have also been used, for which the measured electrode positions are projected onto this surface, all of the measured potentials are used to calculate a spline-interpolation function, and the Laplacian operator is computed analytically from this function for each electrode position. The advantages of the method described here are construction of a realistic and accurate surface model of the head from the measured electrode positions, use of an accurate three-dimensional local spline interpolation function, and a stable numerical integration method of estimating Laplacian values using Taylor expansions and the least significant error minimization technique. Construction of the triangle mesh surface from electrode locations is performed in a stepwise procedure designed for primarily convex surfaces with no folding. In the first step the two closest neighbors of any selected electrode are found which determines the first triangle in the mesh and the current mesh boundary. The next step finds the closest electrode outside the boundary, adds a new triangle, and revises the mesh boundary. This is repeated until all electrodes have been incorporated into this triangle mesh. Also, after each step, a triangle is added using three consecutive electrodes on the boundary, when necessary, to make the boundary edge convex. At the end, all adjacent triangles are also checked to see if an obtuse angle might be reduced by substituting the two alternative triangles. Geometry associated with this electrode and the local potential distribution. In reality only the polygons defined by the given electrode and the surrounding electrodes, and potential values at these points are used.

Local surface construction

For a given electrode, all its surrounding electrodes are found and a sublist of polygons using these electrodes only is formed from the global triangular mesh. If the resulting polygons in the sublist form a complete circle around the given electrode, this point is classified as an internal point and this sublist of polygons as classied as the local surface associated with this given electrode. Otherwise, it is classified as an edge point and no Laplacian Derivation operation will take place for this electrode since the information of local potential distribution around this point is not complete.

Local potential distribution

Potential values at the given electrode and its surrounding electrodes, say n, are used to construct the following local spline interpolation function P(x,y,z) to approximate the local potential distribution function.

$$P(x,y,z) = \sum_{j=0}^{n} a_j/((x-x_j)^2 + (y-y_j)^2 + (z-z_j)^2 + w^2)^{\frac{1}{2}} + a_{n+1}. \quad (1)$$

The coefficients $a_j$ are determined by solving a set of simultaneous linear equations which force the interpolated values at the electrode positions to be equal to the measured potentials, and which satisfies the following:

$$\sum_{k=0}^{n} P(x_k,y_k,z_k) = (n+1) \sum_{j=0}^{n+1} a_j.$$

Function P(x,y,z) defined in Eq.(1) is a spline-like function as it is a linear combination of reciprocals of distances. A nonzero constant w assures that this function is infinitely differentiable. The value of w which has been used is the average inter-electrode distance. The function P(x,y,z) is reference-invariant in the sense that if the measured potentials are re-referenced, the interpolated values change by the same constant.

Laplacian Derivation operation

The Laplacian Derivation operation at electrode $(x_0,y_0,z_0)$ is the following quantity:

$$\Delta V(\xi,\eta) = \nabla \cdot \nabla V(\xi,\eta) = \frac{\partial^2 V}{\partial \xi^2} + \frac{\partial^2 V}{\partial \eta^2} \text{ at } \xi_a, \eta_a,$$

where $x=f(\xi,\eta)$, $y=g(\xi,\eta)$ and $z=h(\xi,\eta)$ is the parametric representation of the local surface reconstructed, and $$x_0 = f(\xi_a,\eta_a); \ y_0 = g(\xi_a,\eta_a); \ z_0 = h(\xi_a,\eta_a).$$

The desired quantities $(\partial^2 V/\partial \xi^2)$ and $(\partial^2 V/\partial \eta^2)$ at $(\xi_a,\eta_a)$ are numerically solved using the three-term Taylor expansions of twelve surrounding points $(\xi_b,\eta_b)$ in its parametric space. They are:

$$V(\xi_b,\eta_b) - V(\xi_a,\eta_a) \approx \frac{\partial V(\xi_a,\eta_a)}{\partial \xi}(\xi_b - \xi_a) + \quad (2)$$

$$\frac{\partial V(\xi_a,\eta_a)}{\partial \eta}(\eta_b - \eta_a)(\xi_b - \xi_a)(\xi_b - \xi_a)/2 +$$

$$\frac{\partial^2 V(\xi_a,\eta_a)}{\partial \eta^2}(\eta_b - \eta_a)(\eta_b - \eta_a)/2 +$$

$$\frac{\partial^2 V(\xi_a,\eta_a)}{\partial \xi \partial \eta}(\xi_b - \xi_a)(\eta_b - \eta_a).$$

In our programming implementation, $(\xi_b,\eta_b)$ are twelve equally-spaced points each at a radial distance $\xi$ from $(\xi_a,\eta_a)$ to guarantee numerical stability when equation (2) is solved by a least-squares method. The function values $V(\xi_b,\eta_b)$ (b=1,2,...,12) are calculated by the local interpolation function $P(f(\xi_b,\eta_b),g(\xi_b,$ $\eta_b$),h($\xi_b,\eta_b$)), and V($\xi_a,\eta_a$) equals P($x_0,y_0,z_0$), which in turn is the measured potential value at the given electrode.

Figure 1A:
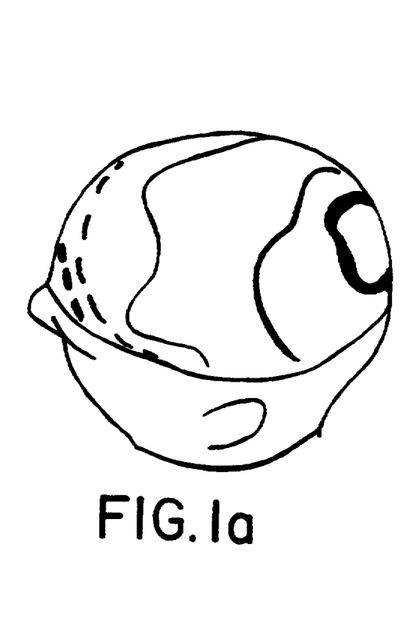
FIGS. 1a and 1b are top plan views of a cross-section of a human head.
Figure 1B:
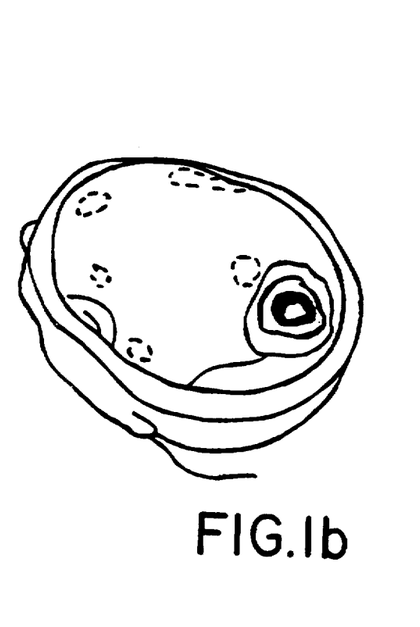

This implementation can be made more efficient for Laplacian operations on an EEG time series by virtue of the fact that, when a triangular mesh is made, the local surface, the structure of the local spline function and the Laplacian Derivation operation for any given internal electrode are fixed. Therefore, a Laplacian weight vector associated with an internal electrode is explicitly constructed which yields the desired Laplacian Derivation when multiplied by the measured potentials on this local surface. FIG. 1 shows the dramatic improvement in spatial detail obtained with this procedure.

DEBLURRING METHOD

A better improvement in distortion correction is possible by using a finite element or surface intergral method to represent the true geometry of cortex, cerebrospinal fluid, skull and scalp, and estimates of the conductivities of these tissues, to model the potential activity described by equations set forth at (1) in the scalp and skull layers. This allows estimation of the potentials which would actually be recorded on the surface of the brain. This can be done without introducing an arbitrary model of the actual number and location of sources because, regardless of where they are generated in the brain, potentials recorded at the scalp must arise from volume conduction from the cortical surface through the skull and scalp.

The finite element method (FEM) is used to compute the numerical forward solutions of this equation as this method is numerically stable and well-suited for handling the complex geometry and varying conductivities of the head. A multidimensional, bipolar vector space optimization scheme is developed to search for the optimal cortical potential distribution whose FEM-based numerical forward solution best fits the actual measured scalp potentials. Since previously, there has been no method of deriving realistic 3-D volumetric finite elements, in accordance with the current invention, we have developed a method for generating finite elements for the entire conducting volume using magnetic resonance images of a subject's head or other measurement means such as mechanical measurement of the shape of the outside of the head and ultrasonic measurement of the thickness of the scalp and skull and outside shape of the brain.

1. Theoretical Formulation

Brain electrical activity may be described by the following Equation (1)

$$\nabla \cdot (\sigma(x,y,z) \nabla u(x,y,z)) = F(x,y,z) \text{ in } \Omega, \quad (1)$$

where $\Omega$ is the conducting volume, $\sigma(x,y,z)$ is the conductivity tensor, $u(x,y,z)$ is the potential distribution function, and $F(x,y,z)$ is the source function within.

For various electromagnetic problems, Eq.(1) coupled with some boundary conditions specified on the surface of $\Omega$ uniquely defines a physical model on $\Omega$. Currently, we choose $\Omega$ as the volume bordered by the scalp surface, denoted by $S_{scalp}$, and the cortical surface, denoted by $S_{cortical}$, extending from the top of the head to a horizontal cut-off surface, denoted by $S_{cut-off}$. To warrant a unique solution to the model, the boundary condition on $S_{scalp}$ is specified as $$\sigma \nabla u(x,y,z) \cdot n = 0 \text{ on } S_{scalp}, \quad (2)$$

since electric current does not flow out of the head in the direction normal to the scalp surface (denoted by n). The boundary condition on $S_{cortical}$ and $S_{cut-off}$ is specified as $$u(x,y,z) = G(x,y,z) \text{ on } S_{cortical} \quad S_{cut-off}, \quad (3)$$

where $G(x,y,z)$ is the cortical potential distribution function. With this kind of choice of $\Omega$, source function $F(x,y,z)$ will be zero everywhere within $\Omega$ since the scalp and skull layers do not contain generating sources. Thus there is no need to determine $F(x,y,z)$.

It is well known that for a given function $G(x,y,z)$, a unique solution $u(x,y,z)$ exists which satisfies Eqs. (1), (2) and (3). This process is often referred to as a forward problem. However, for the Deblurring process, knowledge of $G(x,y,z)$ (one of the required boundary conditions to warrant a unique forward solution) on $S_{cortical}$ is desired in addition to information about $u(x,y,z)$ in $\Omega$. This requirement defines the Deblurring process as an inverse problem, and the usual strategy is employed of using additional apriori information to compensate for the fact that one of the required boundary conditions is unknown. This additional information is used to help find the desired boundary information $G(x,y,z)$ as well as the corresponding forward solution $u(x,y,z)$.

In the EEG application, the measured potential at the scalp surface $S_{scalp}$ provides additional information in the form of an extra boundary condition. That is $$u(x,y,z) = U(x,y,z) \text{ on } S_{scalp} \quad (4)$$

where $U(x,y,z)$ is the potential distribution measured at the scalp. A function $G^*(x,y,z)$ is taken as the desired solution to a Deblurring calculation if the corresponding forward solution $u^*(x,y,z)$ of Eqs.(1), (2) and (3) yields the given scalp potential measurement $U(x,y,z)$ at $S_{scalp}$. The function $G^*(x,y,z)$ is obtained through an optimization method which produces a convergent sequence of candidate functions $G_i(x,y,z)$ such that their corresponding forward solutions $u_i(x,y,z)$ of Eqs.(1) and (2) approach the extra boundary condition $U(x,y,z)$ at the scalp surface.

2. Simulation Studies of the Validity of the Deblurring Method

Simulation studies demonstrate the validity of the Deblurring method. A simple conducting volume is used in the simulations for which the scalp potential distributions satisfying Eqs. (2) and (4) and their corresponding cortical potential distributions can be exactly determined analytically. The validity of the Deblurring method for this particular conducting volume can thus be established by comparing the deblurred data computed from these scalp data with the exact cortical distribution.

A multi-layer half-shell model $\Omega_{shell}$ is chosen because it is a first approximation to a realistic head model and the exact solution $u(x,y,z)$ of Eqs. (1), (2), (3) and (4) for the half-shell model can be obtained. For example, when $\Omega_{shell}$ is the upper-half two-layer shell model embedded within a three concentric sphere model, the corresponding three sphere analytical forward solution $v(x,y,z)$ due to some sources within the inner sphere but outside of $\Omega_{shell}$ will be the exact solution $u(x,y,z)$ for $\Omega_{shell}$ when $v(x,y,z)$ is confined to $\Omega_{shell}$. Based on this observation, the following simulation procedure was designed and applied. First, the scalp, skull, and brain surfaces were modeled as top hemispheres with radii of 9, 8.5, and 8 cm, and the conductivity ratios of scalp/-skull and brain/skull were taken to be 80. The scalp and skull volumes constituting the Deblurring region of interest, $\Omega_{shell}$, were regularly subdivided into a total of 432 prism-shaped finite elements, each formed from two triangles located on adjacent spherical surfaces. There were 127 outer scalp points and 127 inner skull points. Second, the three-sphere analytical forward solution v(x,y,z) was formulated for a dipole lying within the inner sphere. Third, the potentials for finite element vertices on the outer hemisphere were calculated by the analytical forward solution v(x,y,z) to constitute the numerical boundary condition of Eq. (4) at the scalp surface. Fourth, the finite elements generated were used to discretize Equation (1), and the potentials for finite element vertices on the inner hemisphere were solved by the Deblurring method. Finally, the exact potentials for these same vertices were calculated from the analytic solution v(x,y,z), and these potentials were v(x,y,z), and these potentials were compared with the deblurred ones.

The chosen deblurring region $\Omega_{shell}$, which is embedded within a three-sphere model, allows use of the three-sphere analytic solution to generate various kinds of exact scalp data and cortical data from some source located outside of the Deblurring region so that the computed data from the Deblurring method can be compared with the exact data. Table I presents the error ratio of the computed cortical potentials deblurred from the given scalp potentials and the exact cortical potentials produced by six specifically chosen current dipoles. These dipoles vary in depth, orientation, and vicinity in relation to the simulated Deblurring region, and they generate a variety of scalp potential patterns. Positions and orientations of the dipoles are tabulated in spherical coordinates $(\rho,\phi,\theta)$, where $\rho$ is the eccentricity, $\phi$ is the azimuth angle and $\theta$ is the inclination angle. The first column of Table I (dipole type) provides a descriptive summary of each dipole's position and orientation. In this table, if the $\phi,\theta$ components of the dipole's position is equal to the dipole's orientation, the dipole is "radial;" otherwise it is "tangential." If the dipole is located close to the Deblurring region, it is a "peripheral" dipole; otherwise it is "central." If the dipole's position is no more than 1.0 cm from the simulated cortical surface it is "superficial," if greater than 1.0 cm it is "deep." The error ratio is defined as $$\text{error ratio} = \frac{\sum_{k=1}^{127} (V_{computed}(k) - V_{exact}(k))^2}{\sum_{k=1}^{127} (V_{exact}(k))^2}.$$

As can be seen in the table, the error measure ranges from 0.2% to 1.2%. Inspection of the data suggests that the most obvious differences between the deblurred and actual cortical data are due to the inexact numerical approximation of the cortical surface produced by the large finite elements. Overall, the simulation results demonstrate that the deblurred data match the theoretical data quite well.

3. Deblurring on a Realistic Head Model

The Deblurring procedure becomes more complicated when the region to be deblurred, $\Omega$, is a realistic multi-layer head model,

3.1. Finite Element Modeling of Scalp and Skull Layers

Figure 2A:
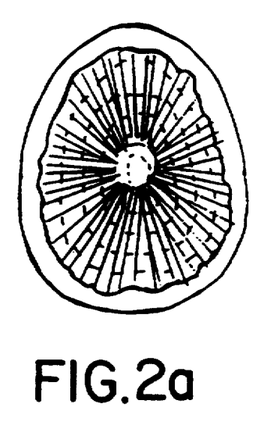
FIGS. 2a and 2b show a single horizontal magnetic resonance image (MRI), at FIG. 2a, after the outer surface of the scalp, skull and brain have been contoured (small circles). (The rings of circles on the inner surface of the brain do not attempt to outline sulci and gyri.) The resulting finite elements constructed from these contours are shown at FIG. 2b with alternating elements shown for brain, skull and scalp volumes, respectively.
Figure 2B:
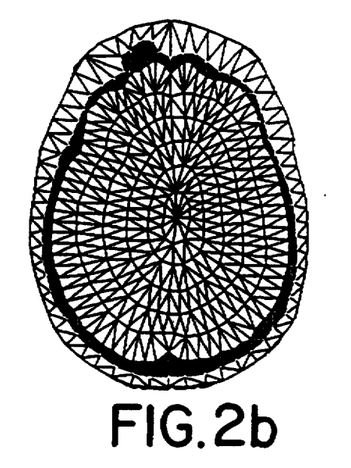
Figure 3A:
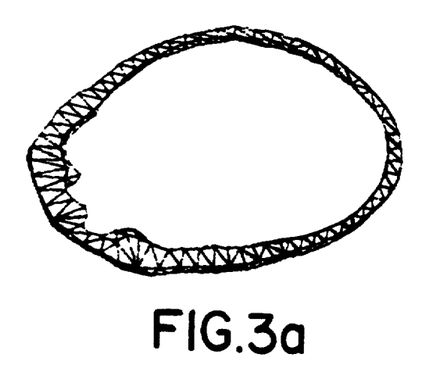
FIG. 3a is a single ring of scalp.
Figure 3B:
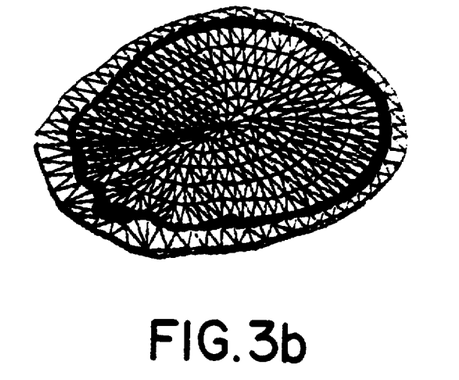
FIG. 3b shows the addition of skull and brain elements within one slice bounded by two consecutive horizontal MR images.
Figure 3C:
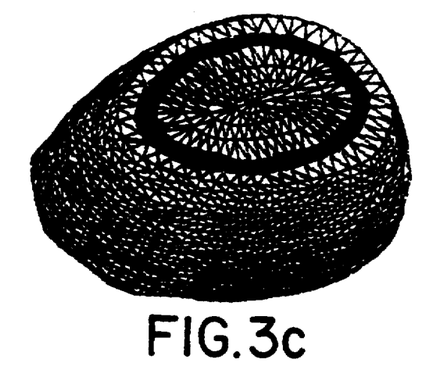
FIG. 3c shows all slices except for the topmost horizontal slice.
Figure 3D:
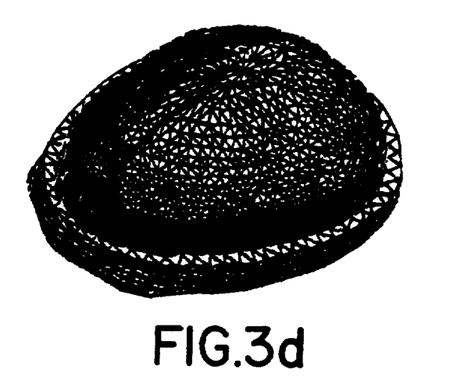
FIG. 3d shows of all three surfaces superimposed.

A crucial first step is to represent the region of interest as a set of similar-shaped volumetric finite elements so that Equation (Eq. (1)) can be discretized, using these finite elements, into a system of simultaneous equations. We developed a procedure for generating tetrahedral finite elements as this shape is well-suited for modeling the complex geometry of the head. In practice, horizontal magnetic resonance image (MRI) slices are first inspected on a workstation to determine the most ventral (bottom) image. Sixty-four radial lines emanating from the center point are superimposed onto the image to guide interactive placement of contour points so that each contour has consistent inter-point spacing (FIG. 2). Contours are generated to delineate the scalp/exterior border, the skull/scalp border, and the brain/-skull border. Finite elements are automatically constructed from the contours in the following manner. For each point on a given contour for a given MRI slice, edges are formed between that point and: (a) adjacent points on the same contour for the same slice, (b) the homologous point and the next point lying on an adjacent contour of the same slice, (c) the homologous point and the next point lying on the same contour of an adjacent slice, and (d) the homologous point and the next point lying on an adjacent contour of an adjacent slice. Triangular faces are formed from the edges and tetrahedrons are formed from the faces. These tetrahedrons, which partition the entire volume, constitute the finite elements (FIG. 3).

3.2. FEM Deblurring Calculations

Figure 4:
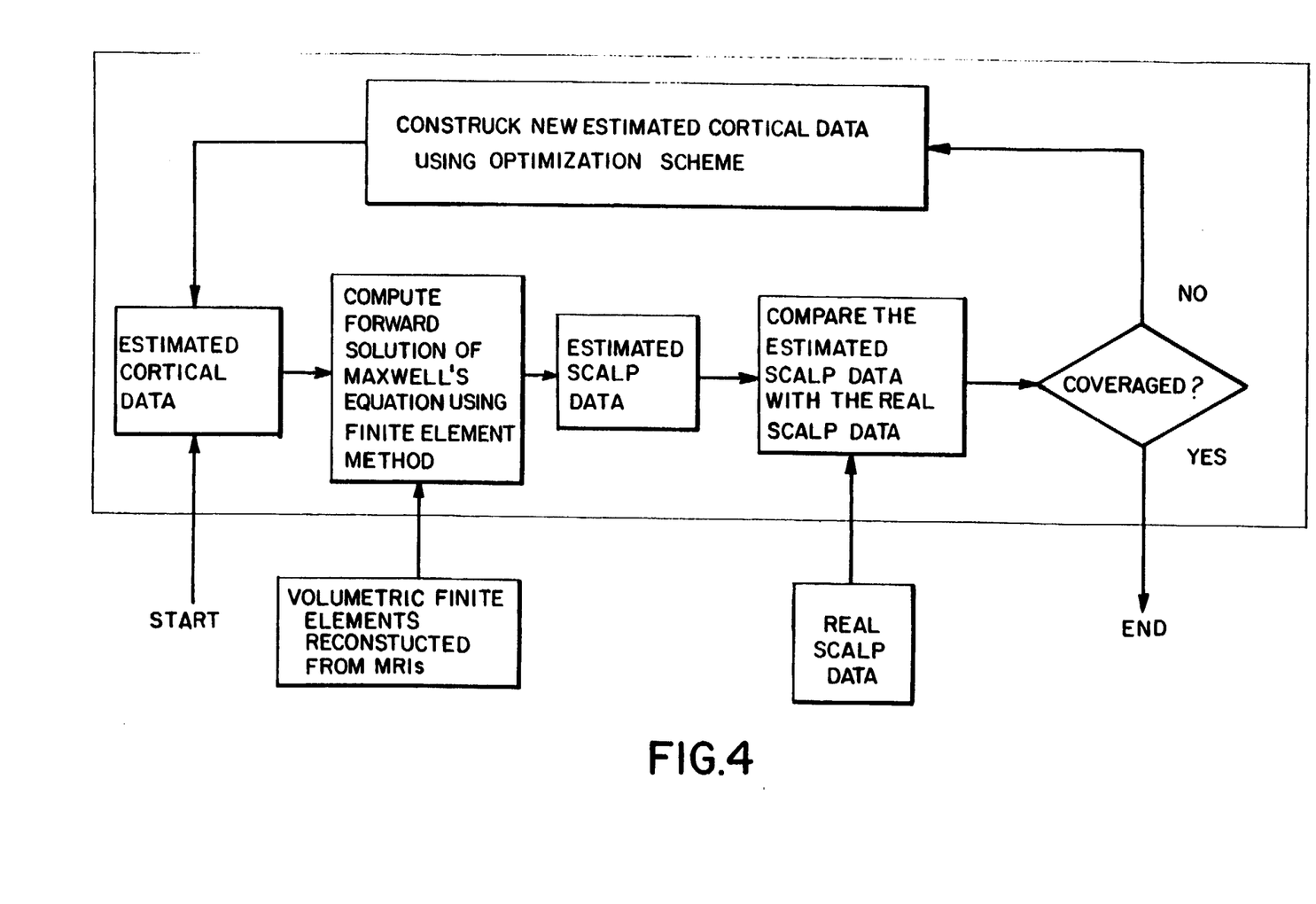

The Deblurring procedure is summarized in FIG. 4. Starting with an initial estimate of the cortical potentials, $G_0 (x, y, z)$, a forward solution of equation (1) is computed using the FEM. This produces an estimate of the scalp potentials which is compared with the actual measured scalp data. The procedure ends if the goodness of fit reaches an acceptable criterion; otherwise, the multidimensional optimization scheme searches for a better estimate of the cortical potentials and the loop contained inside the large frame in FIG. 4 is repeated until convergence is reached.

TABLE I

| | Simulation Results | | |
|---|---|---|---|
| dipole type | dipole position $((\rho,\phi,\theta)$ | dipole orientation $(\phi, \theta)$ | error ratio |
| a) peripheral, radial, (superficial) | (7.0 cm, 0°, 70°) | (0°, 70°) | 0.008986 |
| b) peripheral, tangential, (superficial) | (7.0 cm, 0°, 70°) | (90°, 90°) | 0.007276 |
| c) peripheral, tangential, (superficial) | (7.0 cm, 0°, 70°) | (180°, 20°) | 0.011622 |
| d) central, tangential, (very superficial) | (7.2 cm, 0°, 0°) | (0°, 90°) | 0.003785 |
| e) central, tangential, (superficial) | (7.0 cm, 0°, 0°) | (0°, 90°) | 0.008707 |
| f) central, tangential, (deep) | (5.0 cm, 0°, 0°) | (0°, 90°) | 0.002460 |

Deblurring is comprised of three main computational tasks. First the FEM is applied to a conducting model composed of tetrahedral elements to find a numerical forward solution $u(x, y, z)$ of Eq. (1) with boundary conditions specified in Eqs. (2) and (3) through a transformation matrix approach. Second, a sparse solver is used to find the initial numerical cortical potential distribution function $G_0(x, y, z)$. Third, an efficient multidimensional optimization scheme is employed that searches for an optimal cortical potential map $G^*(x,y,z)$ through construction and testing of a sequence of candidate functions $G_i(x,y,z)$ at $S_{cortical} \cup S_{cut-off}$ to find the one whose numerical forward solution $u^*(x,y,z)$ best fits the given measured scalp potential data.

Before the FEM can be applied, the potentials measured at a relatively small number of scalp sites, say 124, must first be interpolated onto the scalp surface, which consists of some hundreds of vertices of the tetrahedrons. These interpolated potential measurements at the scalp are compared with the solution at each step of the Deblurring procedure. If the potential distribution on $S_{scalp}$ is denoted as $U(x,y,z)$ (the extra boundary condition), the function values of $U(x,y,z)$ at 124 points on $S_{scalp}$ are experimentally defined by the recorded data $U_i$. A spline-like function $$P(x,y,z) = \sum_{i=1}^{124} a_i / ((x - x_i)^2 + (y - y_i)^2 + (z - z_i)^2 + w^2)^{\frac{1}{2}} + a_{125}$$

is then constructed and its 125 unknown coefficients, $a_i$, are determined using the 124 constraints $U_{sub\ i} = P(x_i, y_i, z_i)$ and the constraint that $$\sum_{i=1}^{124} U_i = 124 \sum_{j=1}^{125} a_j,$$

where $(x_i, y_i, z_i)$, $i=1,2,\ldots,124$ are the channel positions, $U_i$, $i=1,2,\ldots,124$ are the directly measured scalp potentials, and $w$ is the averaged inter-electrode distance. Having $P(x,y,z)$, the numerical approximation to function $U(x,y,z)$, the potentials for every finite element vertex on the MRI-determined scalp surface $S_{scalp}$ are estimated, and in so doing, the boundary condition in Eq.(4) is numerically established for the Deblurring procedure to proceed.

Forward solutions using the transformation matrix

Applying the finite element method to Eq. (1) with boundary conditions in (2) and (3), and using standard conductivity values for individual finite elements, the following matrix vector relation is obtained $$Cu = 0. \tag{5}$$

Here C is the global conductance matrix and u is a vector of dimension $\eta_{total}$, which is a numerical approximation to the continuous potential distribution function $u(x,y,z)$ defined in the Deblurring region $\Omega$. The value of $\eta_{total}$ corresponds to the total number of vertices on all the finite elements in $\Omega$. Next, u is partitioned into three parts, which correspond to those vertices on $S_{scalp}$, on $S_{cortical} \cup S_{cut-off}$, and the remaining vertices within the Deblurring region, denoted by $u_1$, $u_3$ and $u_2$ respectively. If the matrix C is partitioned correspondingly, Eq. (5) becomes:

$$\begin{pmatrix} C_{11} & C_{12} & C_{13} \\ C_{21} & C_{22} & C_{23} \\ C_{31} & C_{32} & C_{33} \end{pmatrix} \begin{pmatrix} u_1 \\ u_2 \\ u_3 \end{pmatrix} = 0. \tag{6}$$

When $G(x,y,z)$ is given at $S_{cortical} \cup S_{cut-off}$, i.e., $u_3$ is known, Eq. (6) is rearranged into $$\begin{pmatrix} C_{11} & C_{12} \\ C_{21} & C_{22} \end{pmatrix} \begin{pmatrix} u_1 \\ u_2 \end{pmatrix} = - \begin{pmatrix} C_{13} \\ C_{23} \end{pmatrix} u_3. \tag{7}$$

The resulting vectors $u_1$ and $u_2$ constitute the standard forward solution of Eq. (1) coupled with Eqs. (2) and (3) for a given $G(x,y,z)$ (or for a given $u_3$). Eq. (7) is the numerical representation of the underlying biophysical model formulated above.

During the Deblurring process, a sequence of forward solutions is produced with the same set of finite elements but different cortical candidate maps (or different $u_3$'s). Thus, it is most efficient if the desired forward solution can be derived by simply applying a fixed matrix to a given cortical potential map. Actually, only the partial forward solution at the scalp surface is needed, which is compared to the measured potential at the scalp (the extra boundary condition). This calls for a special-purpose method that reduces the time required for solving a forward solution at each step to that for a simple matrix-vector multiplication at each step. It can be shown that if the coefficient matrix of Eq. (7) is inverted and the inverted matrix is premultiplied to both sides of Eq. (7), the top half of the resulting matrix on the right side can be extracted to yield the desired partial forward solution $u_1$ for a given $u_3$. This transformation matrix is denoted by A. $u_1 = Au_3$. Because matrix A is derived from the matrix manipulation of the global conductivity matrix C defined in Eq. (6), which is invariant for a fixed finite element model representing $\Omega$ and for a given set of conductivity values identifying various tissues within $\Omega$, matrix A can be used to repeatedly derive forward solutions in the Deblurring process for the same subject. For a particular model of dimensionality 1886, our sparse solver uses 0.34 Mflops and 0.128 Mbytes to construct matrix A, whereas a standard Cholesky Method requires 1118 Mflops and 28.5 Mbytes to obtain the same solution.

Multidimensional optimization

The Deblurring method is essentially a multidimensional optimization scheme that searches for an optimal cortical potential distribution whose forward solution best fits the measured scalp potential distribution. In practice, the search starts with $G_0(x,y,z)$, computes the corresponding forward solution $u_0(x,y,z)$, and measures the goodness of fit between $u_0(x,y,z)$ and the measured $U(x,y,z)$ at the scalp surface. $G_1(x,y,z)$ is then sought by the optimization scheme using the goodness of fit measurement and the process is repeated. The iterative process is stopped at step $i_0$ when $G_{i_0}(x,y,z)$ produces a forward solution that is acceptably close to $U(x,y,z)$.

The first step in the optimization scheme is choosing a good starting point for $G_0$ that is fairly close to $G^*(x,y,z)$. The closer $G_0$ is to $G^*(x,y,z)$, the fewer the iterations that will be needed to find a forward solution u(x,y,z) acceptably close to U(x,y,z). We rearrange Eq. (6) into $$\begin{pmatrix} c_{22} & c_{23} \\ c_{32} & c_{33} \end{pmatrix} \begin{pmatrix} u_2 \\ u_3 \end{pmatrix} = - \begin{pmatrix} c_{21} \\ c_{31} \end{pmatrix} u_1 \tag{8}$$

and use the measured potential U(x,y,z) in Eq.(4) as $u_1^{(0)}$ to solve for $u_3^{(0)}$. The solution of Eq. (8) is the forward solution of Eq. (1) coupled with boundary condition (4) on $S_{scalp}$ and boundary condition (2) on $S_{cortical} \cup S_{cut-off}$. This is an auxiliary system to the forward solution system and the corresponding forward solution $u_3^{(0)}$ provides a reasonable starting point for the proposed optimization scheme.

For a given transformation matrix A and a starting vector $u_3^{(0)}$ (the numerical representation of the initial cortical potential distribution function $G_0(x,y,z)$), the goal of the iterative process is to find a vector $u_3^*$, which is the numerical representation of function $G^*(x,y,z)$, such that the resulting goodness of fit is maximized. The dimension, n, of the vector $u_3^*$ is the total number of MRI-derived finite element vertices on the cortical and cut-off surfaces. If we define $G_i(=u_3^{(i)})$ as the numerical representation of $G_i(x,y,z)$ at step i, then each $G_i$ can be visualized geometrically as the location of a point in $R^n$. The following optimization algorithm describes an iterative procedure for finding the numerical function $G_i$ given $G_{i-1}$ and its corresponding goodness of fit.

1) An n-dimensional hypercube of radius $\sqrt{n}r_i$ is created with $G_{i-1}$ at its center. (An initial radius value, $r_1$, is supplied as a parameter to the algorithm. This starting radius is chosen by computing the mean of the scalp potentials.)
2) A point, chosen from the possible $2^n$ candidates populated on the surface of this hypercube, is found in the inner iterative stage such that $G_{i-1}+\Delta G_{i-1}^k$ maximizes the goodness of fit without testing all of the $2^n$ candidates. $\Delta G_{i-1}^k$ is defined as $$\Delta G_{i-1}^k = (s_1 r_i, s_2 r_i, \ldots, s_n r_i)^t, k=1, \ldots, 2^n, s_j=1 \text{ or } -1, j=1, \ldots, n.$$

Because $s_j$ takes on values of either 1 or $-1$, $\Delta G_{i-1}^k$ is referred to as a bipolar vertex. The inner iterative stage consists of the following:

2.1) Given one initial bipolar vertex on the surface of this hypercube (initially chosen in the same direction as $\Delta G_{i-2}$), the goodness of fit for that vertex and for the n adjacent bipolar vertices is computed.
2.2) If all the goodness-of-fit measures for the n neighbors are worse than the one for itself, the current bipolar vertex is considered the best and the outer stage of iteration is resumed at step 3).
2.3) Otherwise, make the neighboring bipolar vertex with the best goodness of fit the new initial bipolar vertex and go back to step 2.1).
3) If the resulting goodness of fit is better than that for $G_{i-1}$, the vector $G_{i-1}+\Delta G_{i-1}^{(k)}$ is chosen as $G_i$, $r_{i+1}=r_i$.
4) Otherwise the current hypercube is shrunk by half in radius and step 2) is repeated on a reduced hypercube. If the hypercube has not shrunk for three consecutive iterations, the radius of the new hypercube is increased by 75% to speed up the movement of points $G_i$ in vector space $R^n$.

In summary, this search method proceeds by searching for a local optimal point on an intermediate domain, i.e., the surface of an n-dimensional sphere. When a better point is found on the surface, a new n-D sphere with the same radius is set up around this better point and the next better point is sought on the new surface. Otherwise the global optimal point must be contained within the current sphere, in which case the original sphere is shrunk by half and the next better point is sought on the new surface. Efficiency of this technique is achieved by exploiting the fixed structure of the transformation matrix A, and by the selection of the $2^n$ bipolar vectors embedded in the n-dimensional sphere. The advantage of using the $2^n$ bipolar vector structure is not only that these $2^n$ vectors happen to be a set of vertices of a hypercube and therefore, the maximal and minimal points within this hypercube can be estimated by the maximal and minimal points among its vertices, but also that it allows the inner search loop to be executed efficiently.

4. Application to Data from Human Subjects 4.1. Comparison of Estimated and Measured Cortical Data in an Epileptic Patient To verify the results of the Deblurring procedure for a realistic head model, both scalp and cortical averaged evoked potential (EP) data were obtained from an epileptic patient. Deblurring was performed on the scalp data, and the results were compared with the measured cortical data. The MRI-derived finite element model for this subject had 5139 tetrahedral volumetric elements and 1300 vertices, among which 438 were scalp vertices and 393 were vertices at the cortical and cut-off surfaces. The transformation matrix A, therefore, had a dimension of 438 by 393 and the vector space in which the inverse solution was sought had a dimension of 393. FIGS. 5(a–b) show the scalp and cortical brain surfaces for this subject and color isochrome maps of three different sets of EP data. The 15-Hz EP recorded from the scalp (referenced to digitally linked mastoids) is shown on the left side of FIG. 5(a), while the estimated cortical EP calculated via the Deblurring procedure is shown on the right side of FIG. 5(a). The Deblurring results are compared with the actual cortical recording in FIG. 5(b); the grid isochrome map is superimposed onto the (monochrome) cortical surface on the right side of the figure, and the Deblurring results appear on the left. The original scalp EP distribution shows a single, near circular area of maximal potential in the mid-parietal area of the left hemisphere. The deblurred computed cortical EP shows a more compact and irregularly shaped maximum in about the same area, with a polarity reversal towards the midline. The recorded actual cortical EP shows a single, even more compact maxima in about the same area. The computed cortical EP better matches the actual cortical EP than does the original raw EP recorded at the scalp.

Conductivity Variations

This result was based on a standard scalp/skull conductivity ratio of 80. Deblurring calculations were also performed using other values of the conductivity ratio. FIG. 5(c) shows the Deblurring results for ratios of 40, 80 and 120. For these and other values examined, different conductivity ratios produced differences in the size of active regions and in the finer detail but did not dramatically change the overall pattern of activity.

4.2. Deblurring Results for Healthy Subjects

Figure 6B:
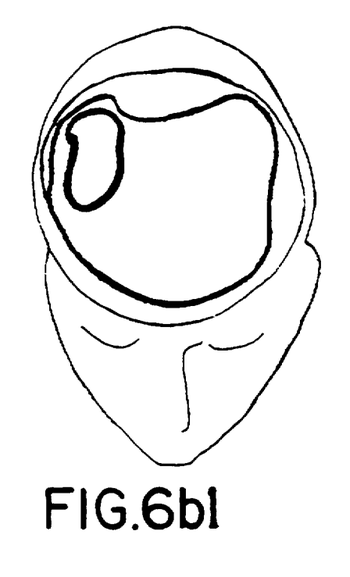
Figure 6B:
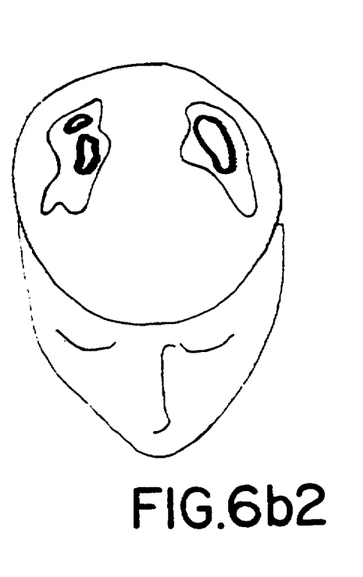

The results of applying the Deblurring procedure to EP data obtained from a healthy subject are illustrated in FIG. 6. FIG. 6(a) shows the results for 15-Hz electrical stimulation of the right index, the right middle, and the left middle fingers. As would be expected, potential maxima are on the side of the cortex that is contralateral to the stimulated hand. Stimulation of adjacent fingers of the same hand produced distinguishable patterns of cortical activation. FIG. 6(b) compares the original EP at the scalp (recorded referenced to digitally linked mastoids) with the deblurred EP for stimulation of this subject's left middle and right index fingers. The increased spatial detail produced by the Deblurring method is apparent.

5. Surface Integral Method

An alternative to performing deblurring (or dipole source localization) through using numerical solutions to the differential form of Equation (1) is to use numerical solutions to the integral form of Equation (1).

The following equation is used for the source localization problem:

$$2\pi\sigma \tilde{x}_0 u - \sum_{i=1}^{I} \int_{S_i - \tilde{x}_0} (\sigma_{i,out} - \sigma_{i,in}) \frac{\hat{n}_i \cdot \hat{R}}{R^2} u = -\frac{\vec{R}_j \cdot \vec{J}}{R_j^3} \quad (9)$$

where $\sigma$ denotes conductivity; $\tilde{x}_0$ is a point on the outer surface of the scalp, u is potential; $\vec{R}_j$ is the vector from a source to $\tilde{x}_0$ and $R_j$ is its magnitude; $\vec{J}$ is the moment of a dipole source; I is the number of interfaces, $S_i$, between regions differing in conductivity; $\hat{n}_i$ is the unit vector from the in region to the out region; and $\vec{R}$ is the vector from $\tilde{x}_0$ to the point of integration with R denoting the unit vector and $\hat{R}$ denoting the magnitude. A numerical solution of this equation involves obtaining a discrete approximation to the integral. Boundary element methods can be used to do this. An alternative is to use efficient integration methods that have been developed for the sphere and methods of computational geometry for projecting a non-spherical surface onto a sphere.

One advantage of using the integral method for source localization is that no nodes are close to the sources, a locus where potential fields vary a great deal. This is problem for the finite element method.

The following equation is used for the deblurring problem:

$$\sum_{i=1}^{I} \int_{S_i - \tilde{x}_0} (\sigma_{i,out} - \sigma_{i,in}) \frac{\hat{n}_i \cdot \hat{R}}{R^2} u = 2\pi\sigma \tilde{x}_0 u \quad (10)$$

where the notation is that for Equation (9). After regularization, the numerical integration techniques used for source localization are applied. An advantage of this formulation when applied to deblurring is that it accounts for the geometry of the whole conductor whereas the finite element technique only accounts for the portion of the conductor that includes the electrodes on the scalp and the tissue immediately below.

6. Estimating Scalp and Skull Thickness for Models

In the finite element or surface integral methods, the local geometry of scalp and skull are each explicitly represented. If a magnetic resonance image or computerized tomography (CT) brain scan is not available, an alternative method of measuring tissue thickness can be used based on low-frequency ultrasound technology.

For a low-resolution representation of skull thickness, the "end echo" in standard echoencephalography is used to estimate the thickness of the skull. This requires placing the ultrasonic probe at a position on the opposite side of the head from the place of desired measurement, normal to the scalp at the probe, and normal to the skull at the place of skull thickness measurement on the opposite side of the head from the probe. Skull thickness at each of the major cranial bones is measured in the following locations:

| cranial bone | position | probe position |
|---|---|---|
| left temporal | T3 | near T4, directly above the ear |
| right temporal | T4 | near T3, directly above the ear |
| frontal (left) | aF1–aF3 | roughly 1 cm below O2 |
| frontal (right) | aF2–aF4 | roughly 1 cm below O1 |
| left occipital | O1 | .2–.5 cm right of FPZ |
| right occipital | O2 | .2–.5 cm left of FPZ |
| left parietal | aP3 | 1 cm below M2, with upward tilt |
| right parietal | aP4 | 1 cm below M1, with upward tilt |

The end-echo consists primarily of the echo due to reflection from soft-tissue to inner skull interface and the echo due to outer skull to scalp interface (followed by a very small scalp-to-air echo). The delay prior to the end-echo varies, according to scalp location and inter-subject variation, roughly from 90 to 120 microseconds. The delay between the echos from either surface of the skull may vary from 1.7 to 5 microseconds. The second echo is attenuated with respect to the first, and requires a gain increase of 2.5 dB per MHz (typical) to be comparable in size to the first. Pulse widths of 0.25 to 1 microseconds are used with burst frequencies of 2 to 10 MHz, adjusted to produce the best discrimination between the two echos.

As necessary, passive receptors are used to scan the area of the intended skull thickness measurement to determined the accuracy of aim of the transmitted beam. When necessary, an average is taken over a small cluster of locations (3 to 6) near the listed probe site, in order to average over the variations in thickness for a given bone near the target area. In those instances when the aimed beam cannot be focused well on the parietal bones, the average thickness of these bones is estimated from normalized data on the relationship between parietal bone thickness and the average thickness of the other bones.

For finer spatial resolution in measurement of skull thickness, a near side detector can be used. It has two to four transmitters adjacent to the transmitter/receiver probe, spaced far enough away so that the critical angle (27 degrees) prevents energy from the adjacent transmitters from entering the skull at an angle that could be reflected back to the probe. The phase and time delay between the adjacent transmitters and the probe is adjusted to minimize the reverberation at the probe. Thus, at the probe site the adjacent transmitters are contributing energy soley throug reflections from the outer skull surface, and in a way to minimize reverberation at the probe. Only energy transmitted by the probe itself can enter the skull and be reflected back to the probe.

The thickness of the near skull can then be measured either by subtracting independent measures of the reflection time from the outer skull surface (adjacent transmitters inactive) and reflection time of the echo from the inner skull surface (reverberation minimization active), or by interferometry. The interferometry option sweeps the sound frequency (readjusting reverbaration minimization for each frequency), and determines the charge in frequency required for one oscillation in the variation in reflected energy due to interference of the inner and outer reflections from the skull. The measured thickness of the skull is one half the speed of sound in the skull divided by the change in frequency required to move through one "interference fringe".

7. Estimating Conductivities

Up to now, estimates of conductivity for the scalp, skull, CSF and brain have been from standard published sources. More accurate values are needed to realize the full benefit of the FEM head model. This can be done by solving for the ratio of skull-to-scalp and skull-to-brain conductivities using the scalp potential distribution produced by a single compact population of neurons, represented as an equivalent current dipole, whose location is approximately known. In one procedure, a steepest-descent, nonlinear, least-squares fit between the measured potentials and the forward solution of an equivalent current dipole in a three-sphere model is performed. The main unknown parameters are the ratios of conductivities of the tissues, as well as the dipole strength (which is not of interest here). The availability of reasonable initial guesses, as well as upper and lower bounds, from existing experimental data result in realistic solutions for the unknown parameters. A highly localized source suitable for this purpose is the somatosensory evoked potential peak at 20 msec produced by mild stimulation of the contralateral median nerve at the wrist. This potential, negative posterior to the central sulcus and positive anterior to it, is generated by a single compact population of neurons oriented tangentially in the hand area of somatosensory area 3b and located about 2.5–3.0 cm below the surface of the scalp. Published values of the amplitude of the cortical potential and the ratio of cortical to scalp potentials are also available. The global conductivity parameter is then adjusted for each of the finite elements in the skull using local skull thickness measures determined from the low frequency ultrasound, MRI or other means.

An alternative method for estimating tissue conductivity is based on measuring the reverse electromotive force produced by eddy currents induced in the tissue by ans applied external field generated by a coil placed against the head of each patient. The magnitude of this emf depends on the conductivity of the tissue and the frequency of the magnetic field, i.e. higher conductivity means more eddy current is induced which gives a larger reverse emf. Very low frequencies induce eddy currents in all tissues whereas high frequencies induce currents only in the tissues closest to the coil. Scanning a spectrum of frequencies yields data from which the conductivities of each tissue type can be computed.

We claim:

1. The method of obtaining and analyzing data recorded from a plurality of electroencephalograph (EGG) electrodes removably and electrically connected to the scalp of a subject, including the steps of:

(a) amplifying brain waves detected at the electrodes, converting the amplified brain waves into digital data and entering the data into computer system means to analyze the data;

(b) measuring a thickness of the skull of the subject, the thickness of the scalp of the subject and the head shape of the subject;

(c) measuring physical locations of the electrodes on the scalp of the subject;

(d) estimating an electrical conductivity of the skull, scalp and cerebral spinal fluid of the subject; and (e) entering measurements derived from (b), the electrode locations derived from (c) and the conductivity estimate derived from (d) into the computer system means to analyze the entered brain wave data.

2. The method of claim 1 and including the step of obtaining the measurements of (b) by magnetic resonance image (MRI).

3. The method of claim 1 and including the step of obtaining the measurements of (b) by computerized tomographic scan (CT).

4. The method of claim 1 and including the step of obtaining the measurements of (b) by an ultrasonic scan.

5. The method of claim 1 wherein in step (e) the EEG electrode positions from (c) are registered with measurements of the scalp from (b) using an iterative numerical procedure which optimally matches each EEG electrode position with nearest scalp surface points.

6. The method of claim 1 in which in step (e) the computer system means uses a numerical finite element or surface integral model of the subject's scalp, skull and brain surface.

7. The method of claim 1 in which the estimate (d) for the skull is estimated using an equivalent current dipole source model of a sensory stimulus whose major area of cortical activation is known.

8. The method of claim 1 in which the estimates (d) are obtained by measuring a reverse electromotive force produced by eddy currents induced by an applied external field generated by a coil placed against the head of the subject.

9. The method of claim 1 and including the further step of generating volumetric elements from medical images.

10. The method of claim 1 wherein in step (e) a numerical method finite element method or surface integral method are used to obtain spatial deconvolution with the following equation:

$$\nabla \cdot (\sigma(x,y,x)\nabla u(x,y,z)) = F(x,y,z) \text{ in } \Omega.$$

where $\Omega$, is the conducting volume, $\sigma(x,y,z)$ is the conductivity tensor, $u(x,y,z)$ is the potential distribution function, and $F(x,y,z)$ is the source function.

11. The method of claim 1 wherein in step (e) measured EEG potential values are interpolated into potential values for scalp finite element points using a local spline interpolation function which is a linear combination of a set of basis functions which are solutions of the following equation:

$$\nabla \cdot (\sigma(x,y,z)\nabla u(x,y,z)) = F(x,y,z) \text{ in } \Omega.$$

where $\Omega$, is the conducting volume, $\sigma(x,y,z)$ is the conductivity tensor, $u(x,y,z)$ is the potential distribution function, and $F(x,y,z)$ is the source function.

12. The method of claim 1 wherein in step (e) a forward solution from brain surface potential values to scalp potential values is performed using a finite element based forward transformation matrix which is solved with a sparse solver method.

13. The method of claim 1 wherein potentials at a brain surface are estimated using a multi-dimensional optimization method to minimize a difference between calculated and actual scalp potentials and a bipolar-vector space implementation is employed.

* * * * *